(12) United States Patent
Dharmesh et al.

(10) Patent No.: US 8,158,608 B2
(45) Date of Patent: Apr. 17, 2012

(54) **BIOACTIVE FRACTION FROM *ZINGIER OFFICINALE* AND A PROCESS FOR THE PREPARATION THEREOF**

(75) Inventors: Shylaja Mallaiah Dharmesh, Mysore (IN); Mugur Nanjudaiah Siddaraju, Mysore (IN)

(73) Assignee: Council of Scientific and Industrial Research, New Delhi (IN)

( * ) Notice: Subject to any disclaimer, the term of this patent is extended or adjusted under 35 U.S.C. 154(b) by 500 days.

(21) Appl. No.: 12/295,413

(22) PCT Filed: Mar. 30, 2007

(86) PCT No.: PCT/IN2007/000131
§ 371 (c)(1),
(2), (4) Date: Sep. 30, 2008

(87) PCT Pub. No.: WO2007/113855
PCT Pub. Date: Oct. 11, 2007

(65) Prior Publication Data
US 2009/0131364 A1    May 21, 2009

(30) Foreign Application Priority Data
Mar. 30, 2006  (IN) .............................. 900/DEL/2006

(51) Int. Cl.
*A61K 31/715* (2006.01)
*A61K 31/732* (2006.01)

(52) U.S. Cl. ............ 514/54; 536/123.1; 536/124; 536/2

(58) Field of Classification Search .................... 514/54; 536/123.1, 124, 2
See application file for complete search history.

(56) References Cited

OTHER PUBLICATIONS

Mahady, G. B., et al. "In Vitro Susceptibility of *Helicobacter pylori* to treatment of Gastrointestinal Disorders." *Phytotherapy Research* (2005) vol. 19, No. 11 pp. 988-991.
Mahady, G. B., et al. "Ginger (*Zingiber officinale* Roscoe) and the Gingerols Inhibit the Growth of Cag A+ Strains of *Helicobacter pylori*." (2003) vol. 23, No. 5A, pp. 3699-3702.
Yoshikawa, M., et al. "Stomachic Princiles in Ginger.III[1]. An Anti-ulcer Principle 6-Gingesulfonic Acid, and Three Monoacyldigalactosylglycerols . . . in Taiwan." *Chemical and Pharmaceutical Bulletin* (1994) vol. 42, No. 6, pp. 1226-1230.
Al-Yahya, M. A., et al. "Gastroprotective Activity of Ginger *Zingiber officinale* Rosc., in Albino Rats." *American Journal of Chinese Medicine* (1989) vol. XVII, Nos. 1-2 , pp. 51-56.
Yamahara, J., et al. "The Anti-Ulcer effect in Rats of Ginger Constituents," *Journal of Ethnopharmacology* (1988) vol. 23, Nos. 2-3, pp. 299-304.

*Primary Examiner* — Shaojia Anna Jiang
*Assistant Examiner* — Michael C Henry
(74) *Attorney, Agent, or Firm* — Ladas & Parry LLP

(57) ABSTRACT

Ulcer is a serious oxidative stress induced disease with complex pathologic events including upregulation of $H^+K^+$ ATPase of parietal cell (PC) membrane, damage of mucin layer around PC, PC-DNA damage etc. The polysaccharide (GRPP) fraction and antioxidant extract (GRAOX) of ginger was examined for their ability to inhibit $H^+ K^+$ ATPase. Results indicated that the inhibition of $H^+ K^+$ ATPase activity which causes acidity in the lumen of the stomach, also exhibited better $H^+K^+$ ATPase inhibition (PPI) at the IC50 of 27.2 μg (GRPP) and 16.5 μg GAE (AOX) respectively than the known antiulcer proton pump blocker Lansoprazole (19.3 μg). Further the antioxidant activity in antioxidant extract (GRAOX) by various assay systems was examined such as Reducing power, Free radical scavenging (FRS), DNA and cytoprotection systems etc. GRAOX exhibited concentration dependent reducing power ability at 5-25 μg equivalent of phenol. FRS activity with $IC_{50}$ of 6.8 μg equivalent of phenol etc. At 0.3 μg level GRAOX offered >80% protection to DNA and against $FeSO_4$-Asc'orbate induced oxidation. The major active phenolic components were identified as Gallic acid/Tannic acid (46%), and Cinnamic acid (51%).

10 Claims, 11 Drawing Sheets

Lane 1. DNA

Lane 2. OX+DNA

Lane 3. 0.2 µg GRAOX+ OX+DNA

Lane 4. 0.3 µg -GRAOX+ OX+DNA

Lane 5. 0.4 µg -GRAOX+ OX+DNA

BIOACTIVE FRACTION FROM ZINGIER OFFICINALE AND A PROCESS FOR THE PREPARATION THEREOF

FIELD OF INVENTION

The present invention relates to a bioactive fraction from *Zingiber officinale* and a process for the preparation thereof. More particularly, the present invention relates to a process for the preparation of potential antiulcer compounds from ginger (*Zingiber officinale*) rhizome. In particular, the invention recites a process for the extraction of water soluble antioxidant (AOX) and pectic polysaccharide (PP) fractions with antiulcer property exhibiting $H^+ K^+$ ATPase inhibition. The present invention is useful for the treatment of ulcer as inhibitor of gastric $H^+ K^+$ ATPase and for the treatment of gastric cancer, which are caused by the conditions such as stress or acid, or *Helicobacter pylon* induced ulcer etc. The isolated components have many uses in food and herbal formulations, as nutraceutical, pharmaceutical etc.

BACKGROUND AND PRIOR ART

*Zingiber officinale* belongs to the family Zingeberaceae, is cultivated in various parts of the world especially India, China, Mexico etc. It is a major spice crop cultivated in India and marketed as fresh and dried spice. It is perennial small grassy plant grown in all season through out the year. Indian ginger is famous for its flavor, texture and taste. More than spices, ginger is considered as tastemaker, drug, appetizer and flavourant. Ginger products are available in a variety of forms like oils, oleoresins, fresh ginger in brine, pickle, candies, syrup etc. Bleached and unbleached powder forms of ginger are also available in the market. India has a predominant position in ginger production and export. In the world market, Indian ginger is popularly known as Cochin ginger and Calicut ginger. The principal buyers are the Middle East, USA, UK and Netherlands. Ginger is commonly used for abdominal bloating, coughing, vomiting, diarrhea, rheumatism etc.

Ginger (*Zingiber officinale*) is cultivated mainly for its root part or rhizome. The proximate chemical composition of ginger has been investigated and has been shown to contain approximately 1-4% of volatile oils, which are the medically active constituents of ginger. The volatile oils consist of bisaboline, cineol, phelladrene, citral, borneal, citronellal, geramial, linalool, limonene, zingiberol, zingiberine, camphene etc. The oleoresin present in ginger is mainly gingerol and shogaol. The phenols detected in solvent extracts of ginger are mainly gingerol and zingerone. Zingibain a proteolytic enzyme is also present in ginger, in addition to other components such as vitamin B6, vitamin C, calcium, magnesium, phosphorus, potassium and linoleic acid etc. The pungency and aroma of ginger has been identified to be mainly due to gingerol, which contains alcohol group of the oleoresin, volatile oil respectively. This makes Ginger a free radical scavenger and its antimutagenic and anti-inflammatory properties, have been documented.

Gastric hyper acidity and ulcers are very common, causing human sufferings today. It is an imbalance between damaging factors within the lumen and protective mechanisms within the gastro duodenal mucosa. Prolonged anxiety, emotional stress, heamorrhagic surgical shock, burns and traumas are known to cause severe gastric irritation finally leading to ulcer and cancer. There are basically three causes for chronic peptic ulcer. One of the causes is hypersecretory status such as Zollinger-Ellisson syndrome where there is a high and uncontrolled production of acid leading to ulcer. Secondly the non steroidal anti-inflammatory drugs which are used for rheumatoid diseases also causes ulcer either as an aggressive factor causing lesions in the gastric mucosa or acting as inhibitor of protecting factors which renders the stomach defenseless to resist its own acid production. The third factor responsible for ulcer is a rod shaped pathogenic bacteria *Helicobacter pylori*, normally exists in human stomach. Upon harboring in the host, generates ammonia due to its strong urease activity thereby causes ulcers.

The concept of management of ulcer disease is fast changing. Treatment was based on the principle that excessive secretion of acid is the reason for ulcer symptoms. Gastric cells called parietal cells secreted the gastric acid. However understanding of the role of histamine, gastrin and acetylcholine in controlling gastric secretion lead to the designing of antiulcer drugs which act as blockers of such receptors. The role of enzymic gastric proton pump with proton potassium ATPase activity is very crucial in varieties of ulcers irrespective of the root cause. Therefore, blockers of proton potassium ATPase has been considered and explored to design antiulcer drugs such as omeprazole and Lansoprazole etc. However they cause lots of side effects especially in presence of nonsteroidal inflammatory drugs, pregnancy, lactation and during alcoholic consumption etc. Current data provides an alternative source for the ulcer cure.

Ginger is used since time immemorial as a dietary component in daily life as a spicy material. Ayurvedic, Chinese and traditional medicine systems have recommended ginger as a medicinal plant. Ayurveda system considered ginger to be a truly wonder drug. Since exhibits analgesic, anti-emetic, aromatic, aphrodisiac, carminative, diaphoretic, digestive, expectorant, nervine, sialagogue and stimulant activity. It is also used against atherosclerosis, as chemotherapy support, against migraine headaches, morning sickness, motion sickness, nausea and vomiting followed by surgery, rheumatoid arthritis etc. Ginger is a classic tonic for the digestive tract. It stimulates digestion and keeps the intestinal muscles tuned. Ginger has been believed to protect the stomach from the damaging effect of alcohol and nonsteroidal anti-inflammatory drugs and this may help to prevent ulcers. In the present study antiulcer activity has been investigated in ginger extract. The potential antiulcer components have also been identified.

Reference may be made to the EP patent No. 0639379 of Feb. 11, 2003, where in, a procedure for the preparation of a ginger root infusion for desensitivity of teeth and gum to temperature changes. This preparation has been used undiluted as a mouthwash or as an additive to tooth paste, ointment, wax etc.

Reference may be made to JP patent No. 9087193 of Mar. 31, 1997 where in, an antihuman immunodeficiency virus agent effective for preventing the crisis of an healing acquired syndrome containing active ingredients in water extract of ginger family has been claimed.

Reference may be made to CN patent No. 390565 of Jan. 15, 2003 where in, a process for extracting the antibacterial active component from *Zingiber officinale* for treating inflammation and thrombocyte coagulation in a liquid form has been determined and this medical product has anti-inflammatory, antibacterial and anticoagulant activity.

Reference may be made to JP patent No. 2002047195 of Feb. 12, 2002 where in they claim the pharmaceutical composition containing active ingredient of ginger. They claimed that this preparation had anti-inflammatory, antiplatelet aggregation and antifungal activity.

Reference may be made to DE patent No. 19859499 of Jun. 29, 2000 where in, a stable ginger extract preparation has been shown to be useful for treating dyspepsia or travel sickness. This preparation contained oil, triglyceride or fatty acid or alcohol stabilizer.

Reference may be made to CN patent No. 1159343 of Sep. 17, 1997 where in, they claim a Chinese medicine preparation for curing stomachache and its composition is constituted by Chinese herbal medicine of aconite, dried ginger, licorice and chrysanthemum flower and has been claimed useful for treating oral cavity ulcers.

Reference may be made to U.S. Pat. No. 6,217,880 of Apr. 17, 2001 where in, a medicament has been developed for treating recurrent ulcer in mouth. and bechet's which was mainly prepared from root of coptis Chinesesis, isatis root, flower of lonicen rhemannia, Lilly bulb, bamboo leaf, coydalis bungeana, chinese wild ginger and ganoderma snake and thunder god vine in certain weight proportions. This medicament has the effect of clearing heat, diminishing inflammation, cooling blood and closing sores etc.

Reference may be made to CN patent No. 1334094 of Feb. 06, 2002 where in, an exterior applying medicine for treating cold and hot injury, bed sore and chronic ulcer has been claimed. The medicine constituted by brown sugar, pig bone oil, poppy cream, ginger juice and lidocaine powder through proportioning.

Reference may be made to CN patent No. 1337243 of Feb. 27, 2002 where in, a health care anticancer powder made up by using five natural plants, garlic, black pepper, paprika, tea and ginger was prepared. They claimed that this product could be made into products like anticancer tea, anticancer pills, anticancer powder, anticancer capsule, anticancer beer etc. This product was also used as plant pesticides, natural skin and hair protecting products as well as plant cosmetics.

Reference may be made to DE patent No. 102517523 of 15-05-2003 where in, they claim administration of ginger preferably as feed additive that can be used for the treatment of inflammation and or pain in horses.

Reference may be made to US patent No. 2004022875 of Feb. 05, 2004 where in, they claim a pharmaceutical composition comprising an effective amount of an extract of lyophilized extract or at least one bioactive fractions obtained from plant flower *Woodfordia fruticosa* along with one or more pharmaceutically acceptable additives or carriers for treating ulcer.

Reference may be made to WO patent No. 03080086 of 02-10-2003 where in, they claimed a novel synergistic herbal composition for the treatment of gastric ulcer. The herbal composition constituted by an aqueous extract *Aegelemarmeles, Withania somnifra, Blechumorientale, Vitis vinifera, Feronia elephantanum, Punica granatum*, 4-9% by wt of an extract from *Zingiber officinale, Piper nigrum, Piper longum* and *Azadirachta indica* along with one or more pharmaceutically acceptable additives or carriers.

Reference may be made to EP patent No. 1281402 of 05-02-2003, where in, they claim a novel method for the extraction of water soluble ginger root extract, which is different from the conventional one substantially free of gingerols serving as a stimulant or pungent ingredient and can be used as a material for cosmetics because of its hair growth inhibition and antipruritic actions.

Reference may be made to the article entitled "gastroprotective effect of Neem (*Azadirechta indica*) bark extract: possible involvement of $H^+ K^+$ ATPase inhibition and scavenging of hydroxyl radical" of Uday Bandyopadhyay et al. In Life sciences in (2002) vol. 71, p2845-2865 where they have reported the antisecretary and antiulcer effects of aqueous extract of Neem (*Azadirachta indica*) bark, and they also reported that the bark extract inhibits of $H^+ K^+$ ATPase in vitro in a concentration dependent manner.

Reference may be made to the article entitled "inhibition of gastric of $H^+ K^+$ ATPase and acid secretion by SCH 28080, substituted pyridyl(1,2a) imidazole" of Bjorn wallmark et al. In J B C in 1987 vol. 262, no. 5 p-2077-2084. Where they have reported a hydrophobic amine SCH 28080, 2, ethyl-8-(phenylmethoxy) imidazo(1,2a) pyridine-3-acetonotrile, inhibits gastric acid secretion in vivo and in vitro and their study on isolated $H^+ K^+$ ATPase showed that the compound inhibited the enzyme competitively with $K^+$, whether ATP or p-nitrophenyl phosphate were used as substrates.

Reference may be made to the article entitled "Purification of an antiulcer polysaccharide from the leaves of Panax ginseng" of Sun X B et. al in Planta Med. in 1992 vol. 58, p-445-448 where they have reported that water soluble crude polysaccharide fraction from leaves and alkaline soluble crude polysaccharide from roots of this plant prevented HCl/ethanol induced ulcerogenesis in mice dose dependently. They have purified pectic polysaccharide of molecular weight mass 16 kDa and were composed of mainly galactose and galacturonic acid with small proportions of rhamnose, arabinose, mannose, glucose and glucuronic acid.

Reference may be made to the article entitled "Gastroprotective activity in ginger *Zingiber officinale* rose, in albino rats" of Al—Yahya M A et al in Am. J. Clin. Med in 1989 vol. 17 p 51-56 wherein they have showed the cytoprotective and gastroprotective effect of ginger in albino rats.

Reference may be made to the article entitled "The antiulcer effect in rats of ginger constituents" of Yamahara J et al in J. Ethanopharmacol in 1988 vol. 23 p 299-304 wherein they have determined the effects of ginger, a pungent stomachic natural medicine, on HCl/ethanol induced gastric lesions in rats.

Reference may be made to the article of Mahady G B et. al in Anticancer Res in 2003 vol. 5A p 3699-3702, where they have demonstrated that ginger root extracts containing the gingerols inhibit the growth of *H.pylori* Cag+ strains in vitro and chemopreventive effects.

Reference may be made to the article of Yoshikawa et.al in Chem Pharm Bull in 1994 vol. 42 p 1226-1230 wherein they have reported that 6-ginesulfonic acid showed more potent anti ulcer activity than 6-gingerol and 6-shogaol.

Reference may be made to the article of Thomson M et. al in Prostaglandins Leukot essent Fatty Acids in 2002 vol. 67 p 475-478 whereby they suggested that ginger could be a used as cholesterol-lowering, antithrombotic and anti-inflammatory agent.

Present invention reports a process for the preparation of antiulcer compounds from ginger (*Zingiber officinale*) rhizome. It indicates the presence of potent antiulcer polysaccharide as well as antioxidants. It is novel in that this is the first report on antiulcer polysaccharide from ginger from India and worldwide. The polysaccharide fraction and antioxidant fractions from ginger have been found to be very effective inhibitors of proton pump activity via $H^+ K^+$ ATPase inhibition (PPI) as well as inhibition of *H. Pylori*. The effective inhibitory concentration ($IC_e$) of ginger polysaccharide and antioxidant is 27.2 and 16.5 µg GAE respectively.

The present invention is also novel in that

The effective $H^+ K^+$ ATPase (PPA) blockers are good antiulcer agents. The known PPA Inhibitors (PPI) poses lots of side effects such as dizziness; nausea, constipation and these drugs are not preferable during pregnancy and lactating mother.

The antiulcer compounds thus reported have the potency of inhibiting ulcer by multiroutes such as inhibition of acid secretion preferably by antioxidants, enhancement of mucosal defense by polysaccharide and inhibition of *H. pylori* and hence may be effective as antiulcer agent.

The antioxidants present in the powder may also offer additional protectivity to the systems against oxidative stress such as lipid peroxidation, cytoprotection, DNA protection etc. polysaccharide thus found in the preparation may ensure the protection of mucin layer of parietal cell also.

OBJECTIVES OF THE INVENTION

The main objective of the present invention is thus to provide a bioactive fraction from *Zingiber officinale* and a process for the preparation thereof.

Yet another objective of the present invention is to provide a process for the preparation of proton potassium ATPase inhibitor that is a potential ulcer blocker.

Yet another objective of the present invention is to provide polysaccharide (GRPP) and antioxidants in water extract of the powder (GRAOX) that are exhibiting potential antiulcer property.

Yet another objective of the present invention is to determine inhibition of *Helicobacter pylori* by GRPP/GRAOX, since *H. pylori* is a major ulcerogen.

Yet another objective of the present invention is to provide evidence for mucosal protection against oxidative injury.

Yet another objective of the present invention is to characterize antiulcer pectic polysaccharide as Arabinoglucan and antioxidants of ginger water extract as gallic acid and cinnamic acid.

SUMMARY OF THE INVENTION

Accordingly, the present invention provides a bioactive fraction from *Zingiber officinale* comprising of pectic polysaccharides constituted by rhamnose (1 to 2%), arabinose (21 to 24%), xylose (6 to 8%), mannose (2 to 3%), galactose (3 to 5%) and glucose (50 to 58), optionally along with the antioxidant fraction constituted by comprising phenolic acids such as gallic acid/tannic acid (42 to 46%), gentisic acid (0.6 to 0.8%), protocatechuic acid (0.5 to 0.6%), Vanillic acid (0.1 to 0.2%), caffeic acid (0.05 to 0.1%), syringic acid (0.1 to 0.2%) and cinnamic acid (48 to 50%).

The invention further provides a process for the preparation of potential antiulcer components from ginger (*Zingiber officinale*) the process steps comprising:

a) pulverizing the ginger rhizome to a particle size of 20 mesh;

b) refluxing the powder obtained from step [a] with chloroform and petroleum ether in a ratio of 1:1 v/v at a ratio of 1:5 w/v followed by air drying the defatted powder;

c) adding 70% ethanol in the defatted powder obtained from step [b] in the ratio of 1:3 w/v and vortexing for 60 minutes for 3 times to remove free phenolics and soluble sugars;

d) centrifuging the mixture obtained from step [c] at a speed of 5000 to 6000 g for a period of 10 to 15 minutes;

e) lyophilizing the supernatant obtained from step [d] to get a dry lyophilized powder (GRAOX) having proton potassium ATPase inhibition (PPI) and antioxidant activity (AOX);

f) air drying the residue obtained from step [d];

g) treating the air dried residue obtained from step [f] with protease [50 U/100 g] in 100 mM phosphate buffer pH 7.4 for 8 to 10 hours at 37° C. and centrifuged at 8000 to 10,000 g for 10 minutes to remove the protein contaminant and to obtain deproteinated residue;

h) boiling the deproteinated residue obtained from step [g] in 50 mM acetate buffer pH 4.6 and treating with 0.25 μ/g thermoamylase for 30 to 40 minutes and centrifuging at 8000 to 10,000 g for 15 minutes;

i) cooling the residue obtained from step [h] with 7 μ/g glucoamylase in 50 mM acetate buffer pH 4 for 1 to 2 hours for complete removal of starchy polysaccharide followed by centrifugation at 8000 to 10,000 g for 15 minutes;

j) boiling the residue obtained from step [i] with 0.05% ammonium oxalate solution for 60 to 180 minutes at 70° C. to isolate pectic polysaccharide (GRPP) rich fraction;

k) concentrating the GRPP rich fraction obtained from step [j] by flash evaporation;

l) dialyzing the concentrate obtained from step [k] against distilled water in a dialysis membrane of 10,000 cut off to remove ammonium oxalate salts;

m) lyophilizing the dialyzed sample obtained from step [l] to get the desired pectic polysaccharide with a yield of ~6% designated as GRPP.

In an embodiment, the said fraction is useful as a potential antiulcer agent.

In another embodiment, the said fraction inhibited proton pump (proton potassium ATPase activity) at a concentration of about 27.2 μg offering 70 to 90% protection and *H. pylori* growth inhibitions.

In another embodiment, the said fraction exhibited mucosal defense activity with 97% protection to parietal cell mucin, which gets damaged during ulcer condition.

In another embodiment, the said fraction exhibited Proton potassium ATPase inhibition with an $IC_{50}$ of 16.5 μg.

In another embodiment, the said fraction is useful as a cytoprotective agent with a DNA protection activity up to 90% by 0.3 μg to 0.4 μg of GAE.

In another embodiment, the said fraction further comprises phenolic acids such as gallic acid/tannic acid (42 to 46%), gentisic acid (0.6 to 0.8%), protocatechuic acid (0.5 to 0.6%), Vanillic acid (0.1 to 0.2%), caffeic acid (0.05 to 0.1%), syringic acid (0.1 to 0.2%) and cinnamic acid (48 to 50%).

In an embodiment, a process for the preparation of antiulcer powder which is constituted by both polysaccharide (GRPP) as well as antioxidants (GRAOX) has been described.

In another embodiment, the effectiveness of inhibition of parietal cell proton potassium ATPase by ginger antioxidants and polysaccharides has been determined.

In another embodiment, the ability of antiulcer powder to inhibit *H. pylori* growth and to protect mucosal defense has been depicted.

In another embodiment, the multimechanistic antioxidant properties/DNA protection have been provided.

In a further embodiment, the lyophilized proton potassium ATPase inhibitory antiulcer powder constituted by phenolic rich fraction (GRAOX) contains 4.8 mg/g to 5.5 mg/g of phenolics.

DETAILED DESCRIPTION OF DRAWINGS

DETAILED DESCRIPTION OF THE INVENTION

Figure 1:
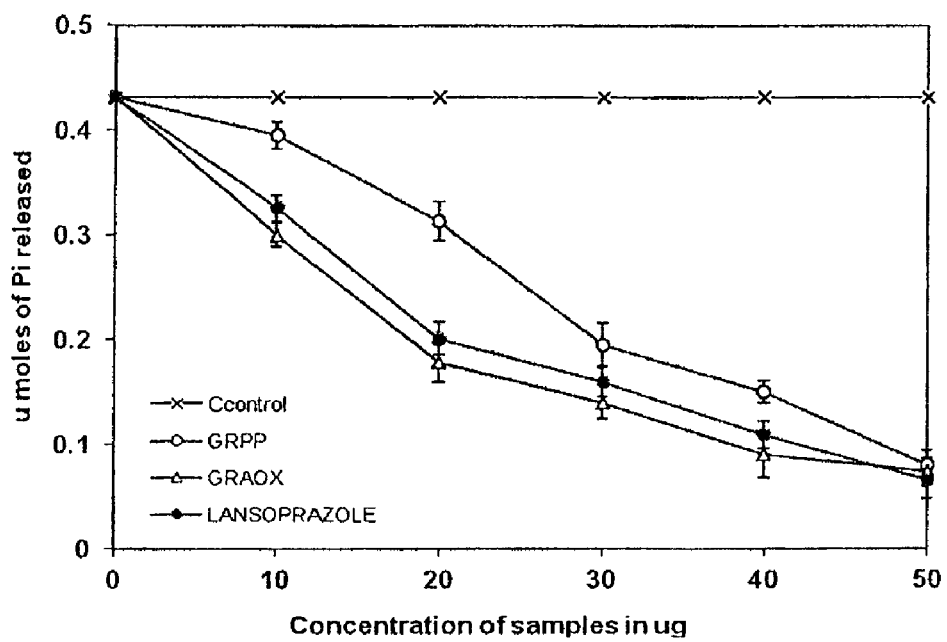
FIG. 1 is a graph showing Proton Potassium ATPase inhibition by Ginger extracts in comparison with Lansoprazole.
Figure 2:
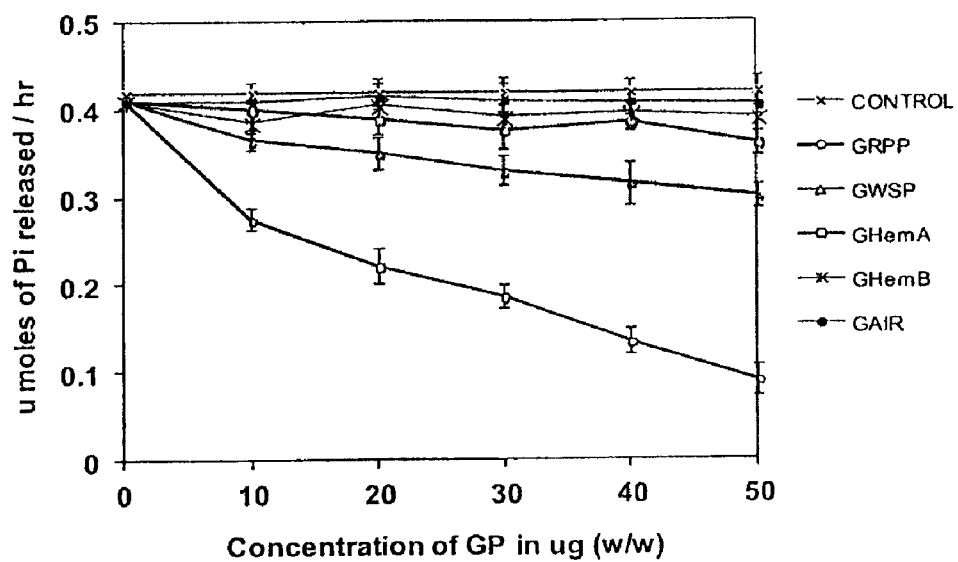
FIG. 2 is a graph showing Proton Potassium ATPase inhibition by Ginger Polysaccharide (GRPP) fractions.

Ginger was purchased from a local market (Devaraja market, Mysore, Karnataka, India). The sample was made into a fine powder. 1 g of defatted (chloroform and petroleum ether, 1:1 (v/v) ginger powder was mixed with 1:3 (w/v) of 70% ethanol and vortexed 3 times, 1 hour each. Residue was separated by centrifugation at 5000-6000 g for 15 min. The supernatant was designated as water extract of ginger (GRAOX) and the residue was further processed for polysaccharide extraction. The residue was air dried and treated with 0.5 U/g of protease from *Aspergillus oryzae* (Sigma chemical co., USA) in 100 mM Phosphate Buffer Saline (PBS), pH 7.4 for 8-10 hours at 37° C. The deproteinated sample was centrifuged at 8000-10,000 g for 15 min to separate the soluble protein and the insoluble polysaccharide. Residue was further treated with termamylase (0.25 U/g, Sigma chemical co., USA) to digest the starch and was digested till it showed negative reaction to the iodine solution. The contents were cooled to 60° C. and then subjected to glucoamylase digestion (7 U/g, Sigma chemical co., USA) for 1-2 hours, centrifuged at 8000-10,000 g for 15 min. The residue was precipitated with 0.05% Ammonium oxalate and boiled for 3 hours; the obtained supernatant was precipitated with ethanol to get pectic polysaccharide (GRPP) (Scheme 1). Residue was processed further to get Hemi cellulose A (GHem A), Hemi cellulose B (GHem B) and Alkali insoluble residue (GAIR) fractions.

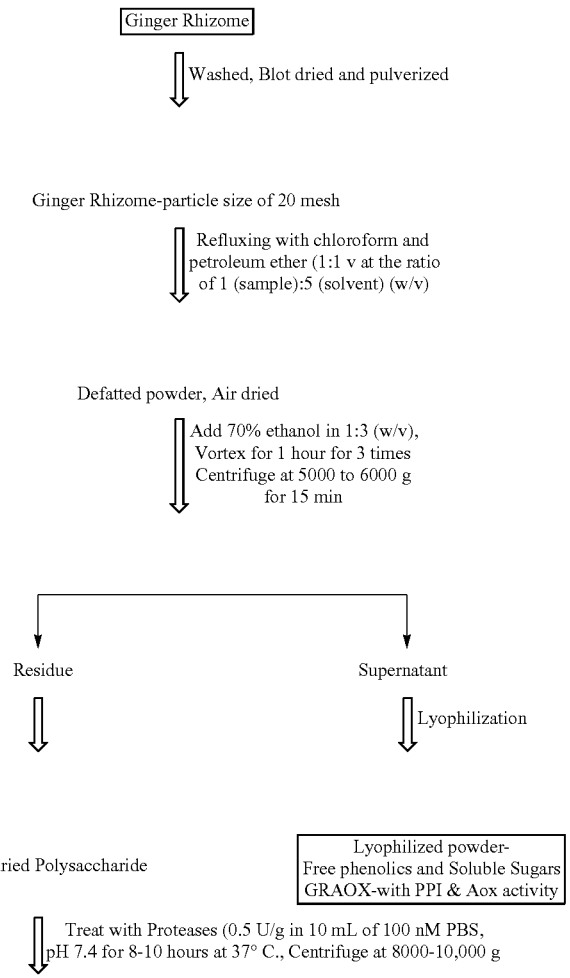

Scheme-1: Preparation of Bioactive Fractions From *Zingiber officinale*

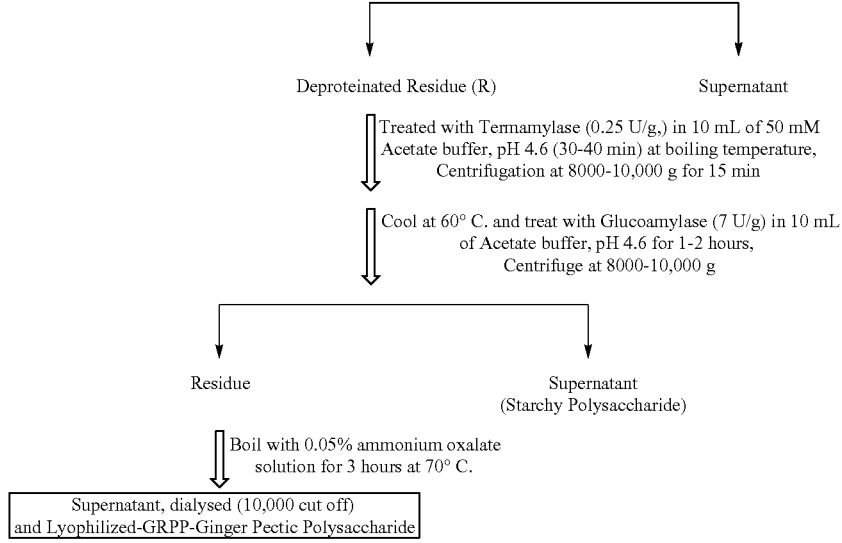

The following examples are given by way of illustration of the present invention and therefore should not be construed to limit the scope of the present invention.

EXAMPLE 1

Preparation of a Potential Antiulcer Powder from Ginger (GRAOX+GRPP)

Ginger was purchased from a local market (Devaraja market, Mysore, Karnataka, India). The sample was made into a fine powder. 1 g of defatted (chloroform and petroleum ether, 1:1 (v/v) ginger powder was mixed with 1:3 (w/v) of 70% ethanol and vortexed 3 times, 1 hour each. Residue was separated by centrifugation at 5000-6000 g for 15 min. The supernatant was designated as water extract of ginger (GRAOX) and the residue was further processed for polysaccharide extraction. The residue was air dried and treated with 0.5 U/g of protease from *Aspergillus oryzae* (Sigma chemical co., USA) in 100 mM Phosphate Buffer Saline (PBS), pH 7.4 for 8-10 hours at 37° C. The deproteinated sample was centrifuged at 8000-10,000 g for 15 min to separate the soluble protein and the insoluble polysaccharide. Residue was further treated with termamylase (0.25 U/g, Sigma chemical co., USA) to digest the starch and was digested till it showed negative reaction to the iodine solution. The contents were cooled to 60° C. and then subjected to glucoamylase digestion (7 U/g, Sigma chemical co., USA) for 1-2 hours, centrifuged at 8000-10,000 g for 15 min. The residue was precipitated with 0.05% Ammonium oxalate and boiled for 3 hours; the obtained supernatant was precipitated with ethanol to get pectic polysaccharide (GRPP (Scheme 1). Residue was processed further to get Hemi cellulose A (GHem A), Hemi cellulose B (GHem B) and Alkali insoluble residue (GAIR) fractions.

EXAMPLE 2a

Determination of Proton Potassium ATPase Inhibition (PPI) by GRAOX and PS Fractions in Comparison with Lansoprazole (PPI inhibitor)

Fresh sheep stomach was obtained from local slaughterhouse at Mysore. The mucosa of gastric fundus was cut off and the inner layer were scraped for parietal cells and homogenized in 16 mM Tris buffer (pH 7.4) containing 10% triton-x100 and centrifuged at 6000 rpm for 10 min. The supernatant (enzyme extract) was used for the assay. Protein content was determined according to Brad ford's method using BSA as standard.

The enzyme extract was incubated with different fractions of ginger, GRAOX and ginger pectic polysaccharide (GRPP) in a reaction mixture containing 16 mM Tris buffer (pH 6.5) and the reaction was initiated by adding substrate (2 mM ATP, 2 mM $MgCl_2$ and 10 mM KCl) and after 30 min of incubation at 37° C., the reaction was stopped by the addition of assay mixture containing 4.5% Ammonium molybdate and 60% Perchloric acid. Inorganic phosphate formed was measured spectrophotometrically at 400 nm. Enzyme activity was calculated as μ moles of Pi released/hr at various doses of GRAOX and GRPP. Results were compared with known antiulcer proton potassium ATPase inhibitor drug lansoprazole. (FIG. 1, Table. 1)

TABLE 1

| \multicolumn{2}{c}{$IC_{50}$ values of GR extracts for Proton Potassium ATPase inhibition} |  |
| --- | --- |
| Sample | $IC_{50}$ value in μg |
| GRAOX | 16.5 μg GAE |
| GPP | 27.2 μg w/w |
| Lansoprazole | 19.3 μg w/w | b. Comparative inhibition of proton potassium ATPase by various polysaccharide fractions of ginger The inhibitory effect of various polysaccharide fractions of ginger on proton potassium ATPase was determined. Ginger pectic polysaccharide (GRPP) fraction was showing the highest inhibition compared with that of other polysaccharide fractions of ginger.

EXAMPLE 3

Inhibition of *Helicobacter pylori* by GRAOX and GRPP

*Helicobacter pylori* was obtained by endoscopic samples of ulcer patients from KCDC (Kamataka Cardio Diagnostic Center, Mysore) and cultured on F12 nutrient agar media with 5% FBS at 37° C.

Figure 3:
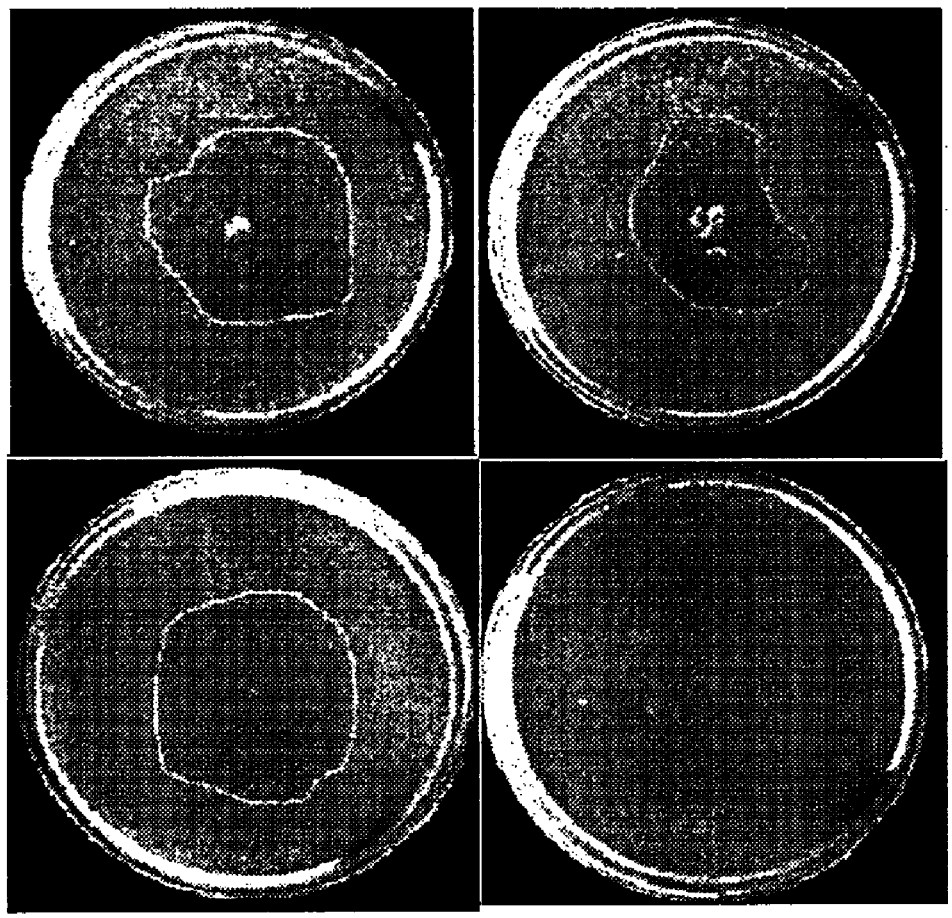
FIG. 3 is a photograph showing gH pylori inhibition zone in presence of A.GRAOX, B.GRPP C.AMOXYPHYLLIN and D. without inhibitor.
Figure 4:
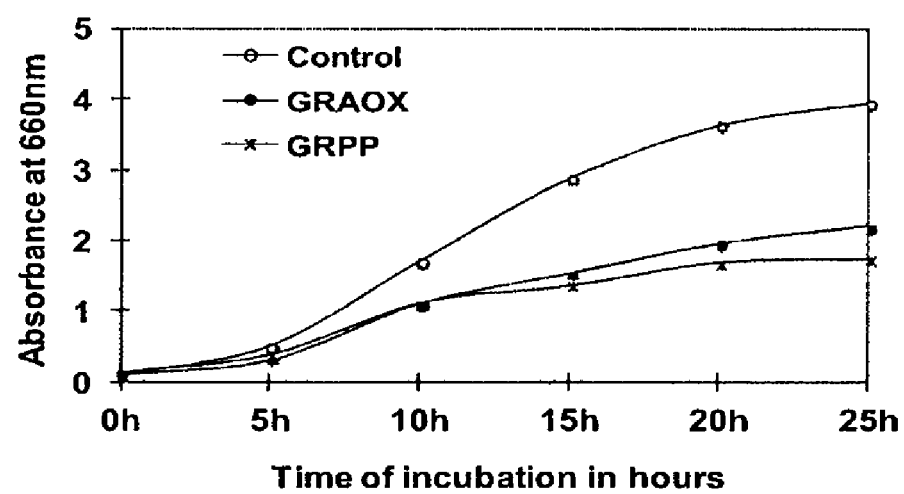
FIG. 4 is a graph showing the inhibition of H pylori growth by GRPP and GRAOX.

*H pylori* grown on nutrient agar plate in presence of GRAOX and GRPP showed a clear inhibition zone around the applied sample at 8 mg and 3 mg concentration (FIG. 3a & b). When *H. pylori* cultured in presence of GRAOX and GRPP in liquid broth media has shown inhibition of growth up to 60% and 75% percent respectively at 5 mg concentration each. Data thus indicate that antiulcer powder prepared has a potential antiulcerogen (anti-*Helicobacter* pylon).

EXAMPLE 4

Effect of GRPP and GRAOX Against Mucosal Defense of Parietal Cells

Figure 5:
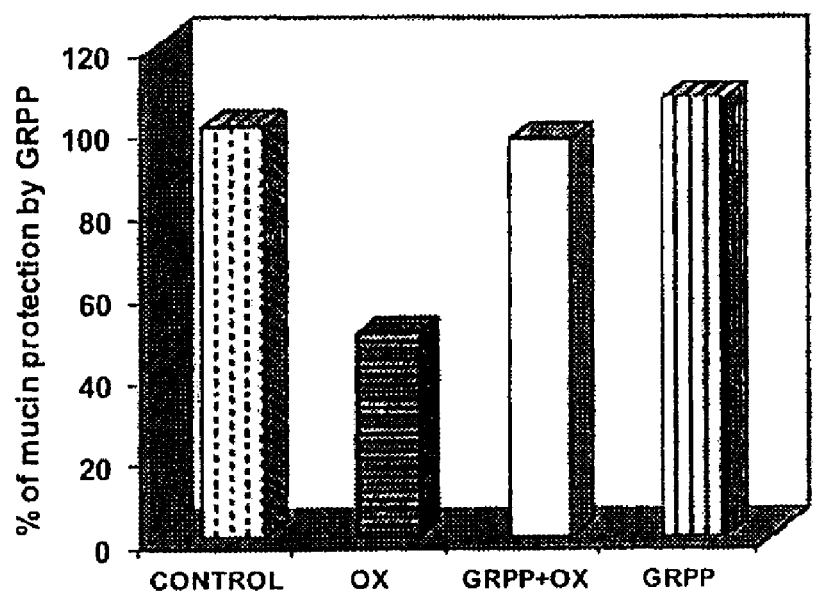
FIG. 5 is a graph protection of mucin layer by GRPP.
Figure 6:
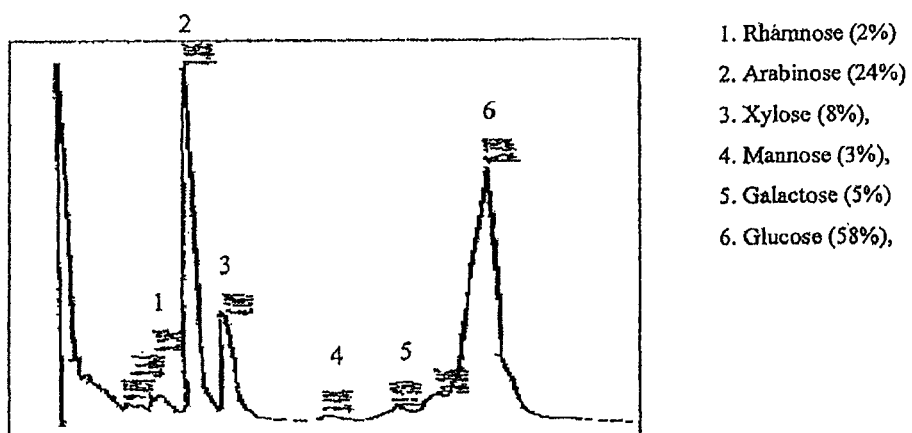
FIG. 6 is a graph showing the GLC profile of GRPP.

The parietal cells in the fundic part of the stomach produce mucus to protect themselves in addition to protect inner stomach lining. Any damage to this mucus layer hence leads to ulcer. In the fallowing assay, mucin was subjected for oxidative stress condition (since it mimics the in vivo situation in ulcer. Fundic part of the sheep stomach membranes were pretreated with and without GRPP extract for 15 min, and subjected to oxidation with 4 mM $FeSO_4$ and 0.1 mM Ascorbic acid for 1 h. After incubation, centrifuged and washed with 0.02M phosphate buffer, pH 7.4 and mucin content was estimated by alcian blue binding assay (U. Bandyopadhyay et al. 2002). Extracts were soaked for 2 h, in 10 mL of a solution containing 0.1% Alcian blue, 0.16M sucrose and 50 mM sodium acetate buffer, pH 5.8. Excess dye was removed by two successive washings in 10 mL of 0.25 M sucrose for 15 min followed the same for 45 min. Dye complexed with adhered mucus was extracted with 10 mL of 50 mM $MgCl_2$ by shaking intermediately for 2 h. Four mL of the extract was then shaken with equal volume of ether until an emulsion is formed. After low speed centrifugation for 10 min, the ether layer was removed and the concentration of the Alcian blue was determined in the aqueous layer by measuring the absorbance at 598 nm. FIG. 5 shows the ~50% reduction in the mucin level in oxidized cells and they were protected up to 97% by GRPP at 200 µg/3 g of stomach membrane.

EXAMPLE 5

Pectic Polysaccharide Sugar Composition Analysis by GLC;

The individual neutral sugar composition of GRPP was determined by hydrolysis of pectic fraction (Selvendran, et al., 1979), followed by derivatization and analysed as their alditol acetates as described by Sawardekar, et al., 1965; York, et al., 1985. and subjected to GLC. Results indicated that GRPP is constituted by Rhamnose (2%), Arabinose (24%), Xylose (8%), Mannose (3%), Galactose (5%) and Glucose (58%),

EXAMPLE 6

Identification of Potential Proton Potassium ATPase Inhibitors in GRAOX

Phenolic content was determined in GRAOX. It contained 5.3 mg gallic acid equivalent (GAE) per gram of ginger powder.

The defatted water extract was analyzed by HPLC for phenolic acids. HPLC system—Shimadzu LC-6A, fitted with C18 column was employed for the analysis.

Figure 7:
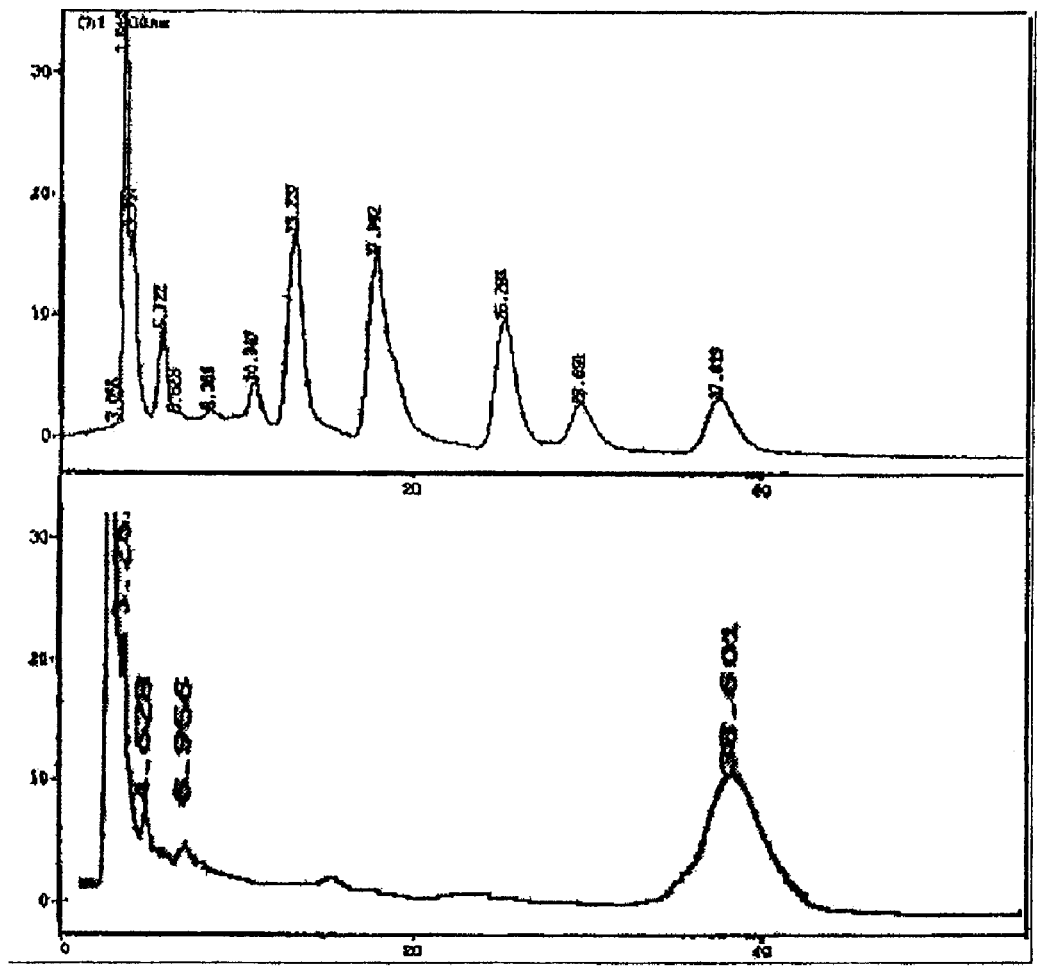
FIG. 7 is a HPLC chromatogram of GRAOX.
Figure 8:
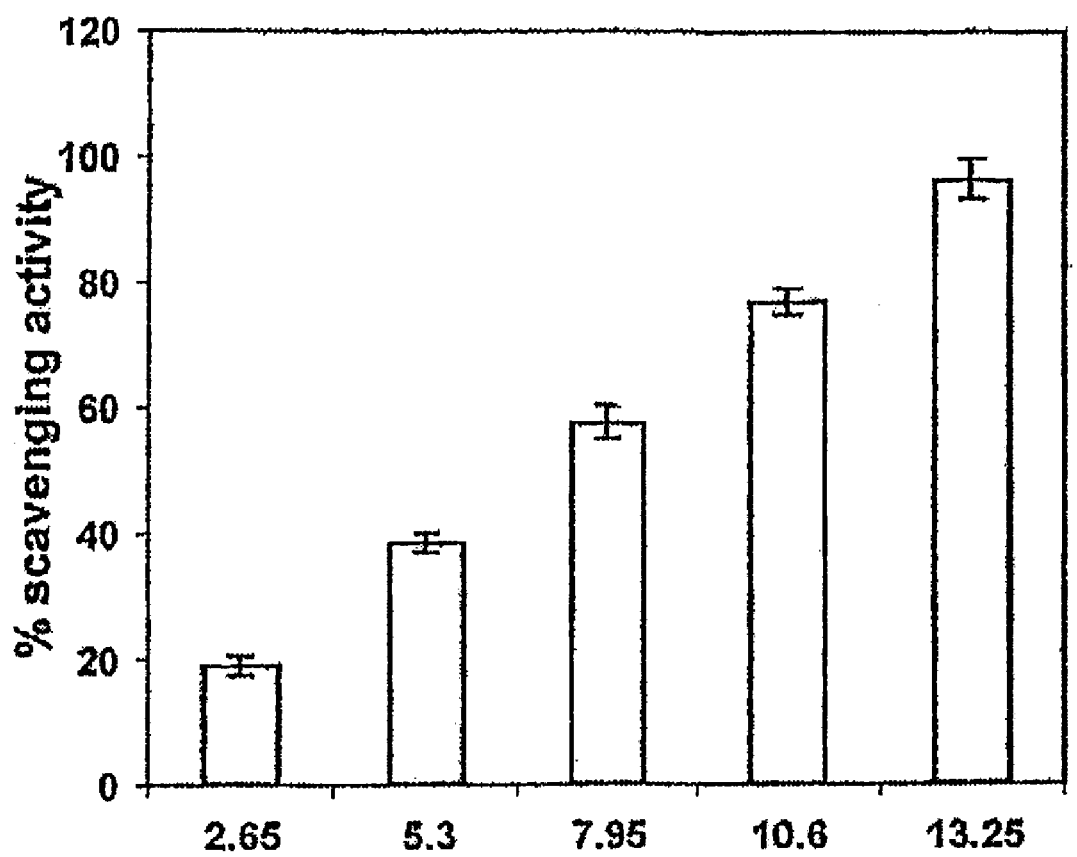
FIG. 8 is a graph showing the free radical scavenging ability of GRAOX.
Figure 9:
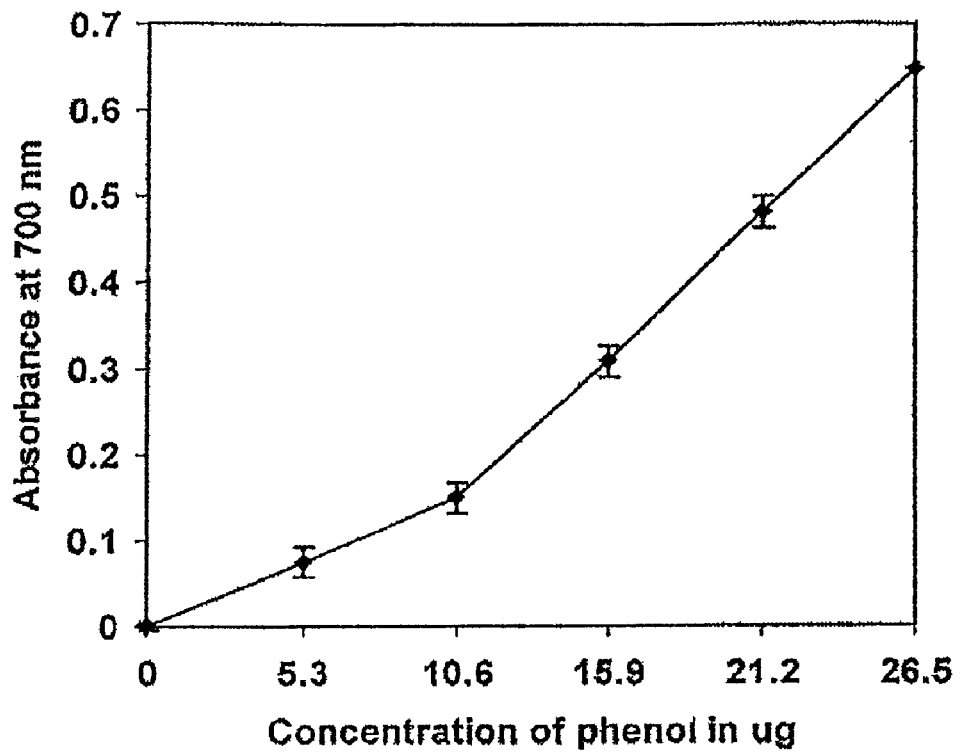
FIG. 9 is a graph showing the reducing power ability of GRAOX.
Figure 10:
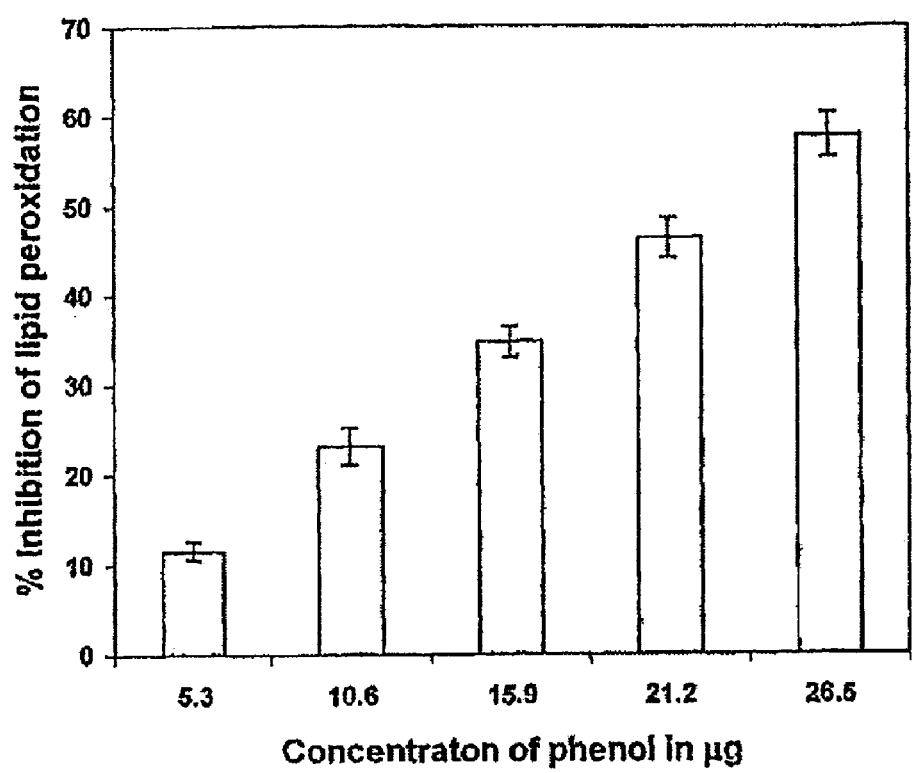
FIG. 10 is a graph showing inhibition of Lipid peroxidation on liver microsomes.
Figure 11:
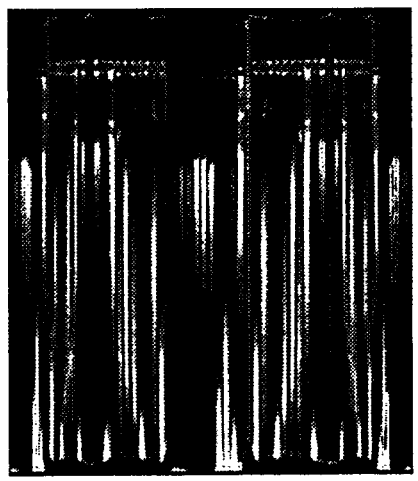
FIG. 11 is a photograph showing protection from DNA damage.

20 µL sample was injected and the emergences of phenolic components were determined using appropriate standards at 280 nm in an UV spectrophotometer. Isocratic elution was carried out in a mobile phase of water: methanol: acetic acid in the ratio of 85: 15: 05 (V/V) with a flow rate of 0.8 mL/min. 20 µL of aqueous extract was injected. Components emerged were identified and Quantitated using standard phenolic acids (FIG. 7). Their retention time and peak area were recorded. Percent abundance was calculated, GRAOX contained significant levels of only gallic acid or Tannic acid and Cinnamic acid (Table. 2).

TABLE 2

Identification of phenolic acids and their percentage of Abundance

| Phenolic acids in GRAOX | Retention time in min | Abundance in % | Aox potency $IC_{50}$ (µg) | Proton potassium ATPase activity $IC_{50}$ (µg) |
|---|---|---|---|---|
| Gallic acid/Tannic acid | 3.5 | 46 | 1.12 | 75.40 |
| Protocatechuic acid | 4.6 | 0.8 | 1.35 | 47.10 |
| Gentisic acid | 6.9 | 0.6 | 1.90 | 59.10 |
| Vanillic acid | 9.8 | 0.2 | 6.60 | 66.60 |
| Caffeic acid | 12.0 | 0.1 | 3.00 | 27.10 |
| Syringic acid | 17.8 | 0.2 | 1.80 | 37.40 |
| Cinnamic acid | 38.6 | 50.4 | 81.0 | 15.12 |

The identified phenolic acids were examined for their ability to inhibit proton potassium ATPase activity and their antioxidant potency was also determined. Cinnamic acid inhibited PPI 8.8 fold better than gallic acid (GA)/tannic acid (TA), however antioxidant potency was ~20 fold higher in GA/TA than Cinnamic acid (Table. 2).

Contribution of active components of GRAOX, Cinnamic acid and Gallic/tannic acid towards the proton potassium inhibition and antioxidant potency was calculated (Table 3).

TABLE 3

Antiulcer and antioxidant attributes of ginger AOX fraction

| Phenolic acids | H+K+ ATPase activity | AOX potency |
|---|---|---|
| Gallic/tannic acid | ~6% | ~92% |
| Cinnamic acid | ~90% | ~2% |
| Other phenolics | ~4% | ~6% |

EXAMPLE 7

Evaluation of Antioxidant Potency of GRAOX

Since PPA inhibition was observed by phenolic acids which are also antioxidants, antioxidant potency of GRAOX was determined by various assays Scavenging Effect of Extracts on DPPH Radical.

The effect of GRAOX on DPPH radical scavenging was measured. An aliquot of GRAOX –200 µL of various concentrations (0.4-2.0 mg/mL) was mixed with 100 mM Tris-HCl buffer (pH 7.4) and then added 1 mL of 500 µM DPPH in ethanol (final concentration of 250 µM). After incubating for 20 min at room temperature in the dark, the absorbance of the resulting solution was measured spectrophotometrically at 517 nm. The capability to scavenge the DPPH radical was calculated using the following equation.

Scavenging effect (%)=(1-Absorbance of sample at 517 nm/Absorbance of Control at 517 nm)×100.

GRAOX at ~2-15 µg of phenol showed 20-100% inhibition with the $IC_{50}$ value of 6.8 µg GAE Measurement of Reducing Power.

The reducing power of GRAOX extract was determined. GRAOX extract (5-25 µg) was mixed with an equal volume of 0.2-M phosphate buffer, pH 6.6 and 1% potassium ferricyanide. The mixture was incubated at 50° C. for 20 min. and an equal volume of 10% trichloroacetic acid was added to the mixture, centrifuged at 6000 rpm for 10 min. The supernatant solution (1.0 mL) was mixed with distilled water and 200 µL of 0.1% $FeCl_3$ and the absorbance was measured at 700 nm. Increased absorbance of the reaction mixture indicated increased reducing power. GRAOX although in crude form, exhibited significant reducing power ability.

Antioxidant Activity on Liver Microsome Lipid Peroxidation:

The microsomes were isolated from the rat liver by a differential ultra centrifugation method. Microsomes (100 µg protein/mL) with different doses of GRAOX were taken in a test tube. The reaction was initiated by the addition of 25 µL of each 4 mM $FeSO_4$, 2 mM ADP, 0.1 mM ascorbic acid and the volume was made up to 1.5 mL with 0.15 M KCl. All tubes were incubated at 37° C. for 30 min. The reaction was terminated by the addition of 2 mL of TBA containing 50% TCA and 0.25 N HCl (TBARS reagent), samples were kept in boiling water bath at 80° C. for 15 min. Malondialdehyde (MDA) formed was measured at 535 nm, and Lipid peroxides were expressed as n moles of MDA formed per mg of protein in presence and absence of 0.75-3 mg of GRAOX. Basal level was calculated without adding co-factor. Assay was compared under similar conditions with a known standard antioxidant.

GRAOX showed inhibition of lipid peroxidation at $IC_{50}$ of 16.8 µg GAE 2.4.4 DNA Protection:

DNA protection activity was performed using calf thymus DNA according to the method of Henry Rodriguez and Steven Akman with little modification. Briefly calf thymus DNA (0.5 µg) was added to Fenton's reagent (0.3 mM $H_2O_2$, 0.5 µM ascorbic acid and 0.8 µM $FeCl_3$) containing 0.02-0.4 µg GRAOX. The final volume of the mixture was brought up to 20 µl and then incubated for 30 min at 37° C. and the DNA was analyzed on a 1% agarose gel followed by ethidium bromide staining.

At the concentration of 0.4 µg, GRAOX showed ~90% protection against DNA damage

Advantages

1. The present invention provides a process for the extraction of water-soluble antiulcer compounds from ginger (*Zingiber officinale*).
2. The present invention also provides a process for the separation of polysaccharides and antioxidants from ginger. Polysaccharides were precipitated and separated by centrifugation. The polysaccharide free supernatant was concentrated to remove ethanol and showed antioxidant property (GRAOX). GRAOX thus were employed for the determination of antioxidant potency. Generally antioxidants are complexed with polysaccharides. Although they exhibit bioactivity in vitro; they are not usually bioavailable. Antioxidant activity of GRAOX was not associated with polysaccharide since its precipitation did not alter the absolute antioxidant activity. The present invention thus has the advantage of isolating both potent polysaccharide free of antioxidant and antioxidant fraction employing a simple steps for separation.
3. The present invention of identifying the multipotent antiulcer activity with multimechanistic routes potentiates the use of ginger polysaccharide and antioxidant fractions of ginger for effective management of ulcer apart from improving the general health.
4. The present invention encourages the use of GRAOX/GRPP in various food, medicinal and herbal formulations, similar to those already prepared employing oil fraction of ginger; since it has the advantage of obtaining easily through decoction without much interferences from other components in ginger.
5. The present invention provides a novel proton potassium ATPase inhibitory antiulcer activity in GRPP and GRAOX. GRAOX showed cytoprotectivity against oxidative stress induced cellular damage. GRPP has the potentials to enhance the mucosal defense, which is perturbed during ulcer. Hence for anti-ulcer herbal and dietary/pharmaceutical formulations, GRPP and GRAOX together with extremely beneficial properties may be employed.
6. The observation on the presence of antiulcer activity and its components in ginger powder may improve the usage, since the scale-up experiments are feasible.
7. The identification of the active component may improve the herbal or dietary formulations, since it can be isolated as naturals and be incorporated rather than the use of crude extract, which may to some extent, dilutes or antagonizes the beneficial effect of GRPP and GRAOX antioxidants.
8. The present invention has the advantage of development of herbal, pharmaceutical and food formulations. Also it may not offer side effects since not many blended varieties are needed in the formulation. Being multipotent, single GRPP/GRAOX with protectant base may be sufficient to fulfill all the needs of health benefits.

The invention claimed is:

1. A fraction from *Zingiber officinale* comprising pectic polysaccharides constituted by 1 to 2% of rhamnose, 21 to 24% of arabinose, 6 to 8% of xylose, 2 to 3% of mannose, 3 to 5% of galactose and 50 to 58% of glucose, optionally along with an antioxidant comprising a phenolic acid selected from the group consisting of 42 to 46% of gallic acid or 42-46% of tannic acid, 0.6 to 0.8% of gentisic acid, 0.5 to 0.6% of protacatechuic acid, 0.1 to 0.2% of vanillic acid, 0.05 to 0.1% of caffeic acid, 0.1 to 0.2% of syringic acid and 48 to 50% of cinnamic acid, wherein the fraction exhibits proton Potassium ATPase inhibition activity, wherein said fraction is obtained by a process comprising:

a) pulverizing ginger rhizome to a particle size of 20 mesh to form a powder;
  b) refluxing the powder obtained from step a) with chloroform and petroleum ether in a ratio of 1:1 v/v at a ratio of 1:5 w/v to form a defatted powder followed by air drying the defatted powder;
  c) adding 70% ethanol in the air dried defatted powder obtained from step b) in the ratio of 1:3 w/v and vortexing for 60 minutes for 3 times to remove free phenolics and soluble sugars;
  d) centrifuging a mixture obtained from step c) at a speed of 5000 to 6000 g for a period of 10 to 15 minutes to form a residue and supernatant;
  e) lyophilizing the supernatant obtained from step d) to get a dry lyophilized powder (GRAOX) having proton potassium ATPase inhibition (PPI) and antioxidant activity (AOX);
  f) air drying the residue obtained from step d);
  g) treating the air dried residue obtained from step f) with 50 U/100 g of protease in 100 mM phosphate buffer pH 7.4 for 8 to 10 hours at 37° C. and centrifuged at 8000 to 10,000 g for 10 minutes to remove the protein contaminant and to obtain a deproteinated residue;
  h) boiling the deproteinated residue obtained from step g) in 50 mM acetate buffer pH 4.6 and treating with 0.25 µ/g thermoamylase for 30 to 40 minutes and centrifuging at 8000 to 10,000 g for 15 minutes;

i) cooling a residue obtained from step h) with 7 μ/g glucoamylase in 50 mM acetate buffer pH 4 for 1 to 2 hours for complete removal of starchy polysaccharide followed by centrifugation at 8000 to 10,000 g for 15 minutes;

j) boiling a residue obtained from step i) with 0.05% ammonium oxalate solution for 60 to 180 minutes at 70° C. to isolate a pectic polysaccharide (GRPP) rich fraction;

k) concentrating the GRPP rich fraction obtained from step j) by flash evaporation to form a concentrate;

l) dialyzing the concentrate obtained from step k) against distilled water in a dialysis membrane of 10,000 cut off to remove ammonium oxalate salts;

m) lyophilizing a dialyzed sample obtained from step 1) to get a desired pectic polysaccharide with a yield of approximately 6% designated as GRPP.

2. A method for the treatment of an ulcer comprising the step of administering a therapeutically effective amount of the fraction of claim 1 to a host in need thereof.

3. The method according to claim 2 wherein the fraction can inhibit proton Potassium ATPase activity by 70 to 90% and can also inhibit *H. pylori* growth.

4. The method according to claim 2 wherein the fraction exhibits mucal defense activity.

5. The method according to claim 2 wherein the fraction exhibits proton Potassium ATPase inhibition with an IC 50 of 16.5 μg.

6. The method according to claim 2 wherein said fraction exhibits a reducing power ability and free radical scavenging ability with an IC 50 of 6.8 μg.

7. The method according to claim 2 wherein said fraction exhibits a DNA protection activity of up to 90% by 0.3 μg to 0.4 μg of gallic acid equivalents.

8. The fraction according to claim 1, wherein said fraction further comprises a phenolic acid selected from the group consisting of 1 to 2% of gallic acid or 1 to 2% of tannic acid, 0.5 to 1% of protocatechuic acid, 1 to 2% of gentisic acid, 5 to 6% of caffeic acid, 3 to 4% of syringic acid, 32 to 34% of p-coumaric acid, and 46 to 48% of cinnamic acid.

9. A method according to claim 2 wherein the administration of said fraction to said host results in cytoprotective activity.

10. The fraction according to claim 1, wherein the fraction comprises the antioxidant and exhibits antioxidant activity.

* * * * *